United States Patent
Wardlaw

[11] Patent Number: 5,948,686
[45] Date of Patent: Sep. 7, 1999

[54] METHOD FOR PERFORMING BLOOD CELL COUNTS

[75] Inventor: Stephen C. Wardlaw, Old Saybrook, Conn.

[73] Assignee: Robert A. Leuine, Guilford, Conn.

[21] Appl. No.: 09/262,552

[22] Filed: Mar. 4, 1999

Related U.S. Application Data

[60] Provisional application No. 60/077,215, Mar. 7, 1998.

[51] Int. Cl.⁶ .................................................. G01N 33/48
[52] U.S. Cl. .................. 436/63; 436/66; 436/70; 436/165; 436/172; 436/177; 435/2
[58] Field of Search ................. 436/63, 66, 70, 436/165, 172, 177; 435/2

[56] References Cited

U.S. PATENT DOCUMENTS

| | | | |
|---|---|---|---|
| 3,916,205 | 10/1975 | Kleinerman | 250/461 |
| 4,004,975 | 1/1977 | Lionetti et al. | 195/1.8 |
| 4,027,660 | 6/1977 | Wardlaw et al. | 128/2 F |
| 4,284,355 | 8/1981 | Hansen et al. | 356/335 |
| 4,594,165 | 6/1986 | Levine et al. | 210/767 |
| 4,790,640 | 12/1988 | Nason | 350/534 |
| 4,940,668 | 7/1990 | Wardlaw et al. | 436/174 |
| 4,950,455 | 8/1990 | Smith | 422/56 |
| 5,397,479 | 3/1995 | Kass et al. | 210/728 |
| 5,427,959 | 6/1995 | Nishimura et al. | 436/534 |
| 5,480,778 | 1/1996 | Levine et al. | 435/7.24 |
| 5,482,829 | 1/1996 | Kass et al. | 435/2 |
| 5,547,849 | 8/1996 | Baer et al. | 435/7.24 |
| 5,585,246 | 12/1996 | Dubrow et al. | 435/7.24 |
| 5,888,184 | 3/1999 | Wardlaw | 494/37 |

*Primary Examiner*—Jill Warden
*Assistant Examiner*—S. Carrillo
*Attorney, Agent, or Firm*—William W. Jones

[57] ABSTRACT

A method for evaluating constituents of a sample of substantially undiluted anti-coagulated whole blood is provided which includes the steps of a) providing a sample chamber; b) admixing a sensible colorant with the sample of whole blood; c) inserting the admixed sample into the sample chamber; d) quiescently holding the admixed sample for a period until rouleaux and lacunae form within the sample; and e) evaluating a target constituent disposed within the lacunae.

8 Claims, 2 Drawing Sheets

METHOD FOR PERFORMING BLOOD CELL COUNTS

This application claims the benefit of the filing date of co-pending provisional patent application U.S. Ser. No. 60/077,215, filed Mar. 7, 1998.

BACKGROUND OF THE INVENTION

1. Technical Field

The present invention relates to methods and apparatus for analyzing whole blood samples, and to methods and apparatus for evaluating constituents within a whole blood sample such as white blood cells, platelets, etc.

2. Background Information

Recent advances in analytical hematology have increased the quantity and quality of information available from a patient's blood sample. As a result, the medical community's interest in using a patient's blood sample as a diagnostic tool has also increased. The methods for analyzing blood samples have not, however, in every case kept pace with the information available. Historically, blood samples have been evaluated by smearing a small amount of undiluted blood on a slide, drying, fixing and staining it, and examining the smear under a microscope. Reasonable results can be gained from such a smear, but the accuracy and reliability of the data depends largely on the technician's experience and technique. In addition, blood smears are labor intensive and cost prohibitive, and are therefore generally not favored for commercial applications.

Another known method for evaluating a whole blood sample involves diluting a volume of whole blood, placing it within a chamber, and manually evaluating the constituent cells within the diluted sample. Dilution is necessary because the number and concentration of the red blood cells (RBC's) in whole blood vastly outnumber other constituent cells. In a sample of whole blood from a typical individual, for example, there are about $4.5 \times 10^6$ RBC's/microliter ($\mu l$) of blood sample, but only about $0.25 \times 10^6$ of platelets and $0.007 \times 10^6$ white blood cells (WBC's) per $\mu l$ of blood sample. To determine a WBC count, the whole blood sample must be diluted within a range of about one part blood to twenty parts diluent (1:20) up to a dilution of approximately 1:256, depending upon the exact technique used, and it is also generally necessary to selectively lyse the RBC's with one or more reagents. Lysing the RBC's effectively removes them from view so that the WBC's can be seen. To determine a platelet count, the blood sample must be diluted within a range of about 1:100 to approximately 1:50,000. Platelet counts do not, however, require a lysis of the RBC's in the sample. A disadvantage of this method of evaluating a whole blood sample is that the dilution process is time consuming and expensive. In addition, adding diluents to the whole blood sample increases the error probability within the sample data.

A modern method for evaluating a blood sample is impedance or optical flow cytometry. Flow cytometry involves circulating a diluted blood sample through one or more small diameter orifices, each adjacent an impedance type or an optical type sensor which evaluates the constituent cells as they pass through the orifice single file. Here again, the blood sample must be diluted to mitigate the overwhelming number of the RBC's relative to the WBC's and the platelets. Although more expedient and consistent than the above described methods, flow cytometry also possesses numerous disadvantages. Some of those disadvantages stem from the plumbing required to carry the sample to, and the fluid controls necessary to control the fluid flow rate through, the sensor means. The precise control of the sample flow is essential to the operation of the flow cytometer. The plumbing within flow cytometers can and often does leak, potentially compromising the accuracy and the safety of the equipment. The fluid flow controls and dilution equipment, on the other hand, require periodic recalibration. The need for recalibration illustrates the potential for inaccurate results and the undesirable operating costs that exist with many presently available hematology analyzers which use flow cytometers. Another disadvantage is the volume of reagents required. Because of the large dilution ratios employed, correspondingly large volumes of liquid reagents are necessary. The large reagent volume increases the cost of the testing and creates a waste disposal problem.

Another approach to cellular analysis is volumetric capillary scanning as outlined in U.S. Pat. Nos. 5,547,849 and 5,585,246 for example, wherein a relatively undiluted sample of whole blood is placed into a capillary of known volume and thickness and is examined while the blood is in a quiescent state. This technique deals with the presence of the RBC's by limiting the scanning wavelengths to those with which the RBC's appear relatively transparent, and it requires that the sample be treated so that the RBC's do not aggregate during the measurement process. Thus, this technique is limited to the use of longer wavelength fluorescence, and there is no provision for the examination of RBC's and platelets or the examination of any cellular morphology.

What is needed is a method and an apparatus for evaluating a sample of substantially undiluted anti-coagulated whole blood that: 1) is capable of providing accurate results; 2) does not require removal of the RBC's prior to analysis; 3) allows the use of a wide range of light excitation sources for sample examination; 4) does not use large volumes of reagents; 5) does not require sample fluid flow during the analysis; 6) is capable of analyzing all or nearly all of the cells and particles in the sample; and 7) is cost-effective.

DISCLOSURE OF THE INVENTION

It is, therefore, an object of the present invention to provide a method for accurately evaluating constituents of a sample of substantially undiluted anti-coagulated whole blood.

It is another object to provide a method and apparatus for evaluating a sample of whole blood that does not require substantial dilutions.

It is another object to provide a method and apparatus for evaluating a sample of whole blood that does not require the use of large volumes of liquid reagents.

It is another object to provide a method and apparatus for evaluating a sample of whole blood that does not require sample fluid flow during the evaluation.

It is another object to provide a method and apparatus for evaluating a sample of whole blood which does not require the removal of the majority of the RBC's prior to analysis.

It is another object to provide a method and apparatus for evaluating a sample which allows the evaluation of all or nearly all the constituents of a sample.

This invention relates to a method and apparatus for use in examining and obtaining information from a quiescent substantially undiluted anti-coagulated whole blood sample which is contained in a chamber. The phrase "substantially undiluted" as used in connection with this invention describes a blood sample which is diluted by no more than about 1:1, and preferably much less. Generally, the only reagents that will be used in performing the method of this invention are dyes, stains and anticoagulants, and these reagents are not added for the purpose of diluting the sample but rather are added to produce a reaction, an effect, or the like that facilitates the test at hand.

According to the present invention, a method for evaluating constituents of a sample of substantially undiluted anti-coagulated whole blood is provided which includes the steps of: a) providing a sample chamber; b) admixing a sensible colorant with the sample of whole blood; c) inserting the admixed sample into the sample chamber; d) quiescently holding the admixed sample within the chamber until rouleaux and lacunae form within the sample; and e) evaluating a target constituent disposed within the lacunae. As used within this specification, the term colorant is defined as any reagent that produces a sensible signal by fluorescent emission, or by absorption of light at a specific wavelength, that can be quantified by the apparatus.

An advantage of the present invention method is that a method for evaluating constituents of a sample of substantially undiluted anti-coagulated whole blood is provided that provides accurate information. Specifically, the present method obviates the need for fluid flow controls and sample dilution, and therefore their associated error probability.

Another advantage of the present method is that constituents within a sample of anti-coagulated whole blood can be evaluated without substantially diluting the sample. The present method requires adding a relatively small quantity of sensible colorant to the whole blood sample, thereby allowing the sample to remain substantially undiluted. The expense and problems associated with dilution are consequently avoided. For example, under the present method useful information can be gained within a 100 μl sample of blood admixed with approximately 10 μl of colorant diluted in saline, or less than 1 μl of dry reagent.

Another advantage is that the present invention method does not require large quantities of reagent when evaluating constituents of a sample of a substantially undiluted anti-coagulated whole blood sample. A person of skill in the art will recognize that decreasing the amount of reagent helps decrease the initial material cost of the analysis and the cost of handling the used reagent after the analysis.

Another advantage of the present method is that sample fluid flow is not required. The present method permits the blood sample to be evaluated while in a quiescent (or "substantially motionless") state. The only motion in the blood sample will be Brownian motion of the formed constituents within the sample, which motion is not disabling of the use of the device of this invention. As a result, plumbing leaks and any environmental and/or safety problems associated with such leaks are avoided. In addition, evaluating the sample while in a quiescent state also obviates the need for fluid flow controls and therefore the cost of procuring and maintaining such controls. A person of skill in the art will recognize the maintenance costs associated with many flow cytometers are considerable, and that avoiding those costs is a clear advantage.

These and other objects, features and advantages of the present invention will become apparent in light of the detailed description of the best mode embodiment thereof as illustrated in the accompanying drawings.

BEST MODE FOR CARRYING OUT THE INVENTION

Figure 1:
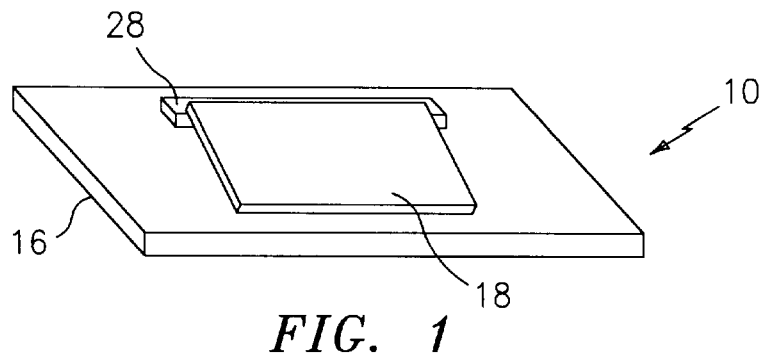
FIG. 1 is a diagrammatic perspective view of a sample chamber.

The method for evaluating white blood cells (WBC's), platelets and other whole blood constituents within a sample of substantially undiluted anti-coagulated whole blood described below provides many advantages over presently available evaluative methods and apparatus. The present method includes the steps of. a) providing a sample chamber 10; b) admixing a sensible colorant with the whole blood sample; inserting the admixed sample into the sample chamber 10; d) quiescently holding the admixed sample within the chamber 10 until rouleaux 30 and lacunae 32 (see FIG. 6) form within the sample; and e) evaluating one or more target constituents within the lacunae 32.

Referring to FIGS. 1–4, the sample chamber 10 includes a first wall 16 and a transparent second wall 18. The walls 16,18 are separated from one another by a through-plane thickness 20 of determinable magnitude. As used herein, the term "through-plane thickness" refers to a line of sight that corresponds to the shortest distance between the interior surface 22 of the first wall 16 and the interior surface 24 of the second wall 18. In a first embodiment (FIG. 2), the walls 16,18 are substantially flat and parallel one another. In a second embodiment (FIGS. 2 and 4), the walls 16,18 converge toward one another, thereby forming a through-plane thickness 20 gradient. The walls 16,18 of the second embodiment may intersect with one another (in which case the through-plane thickness 20 goes to zero) or the walls 16,18 may stay separated by a minimum amount. In a third embodiment (FIG. 3), one or both of the walls 16,18 includes one or more steps 26. Each step 26 creates an independent region having a different through-plane thickness 20. In all embodiments, spacers 28 may be used where appropriate to create/maintain the through-plane thickness 20 between the two walls 16,18, and the walls 16,18 (or step regions 26) may be substantially flat or arcuate.

The through-plane thickness 20 between the walls 16,18 can be determined mathematically and/or optically, or comparatively using a known reference. If, for example, the slope of the walls 16,18 are known and the walls 16,18 are in contact (or separated by a known amount; e.g., a spacer 28), then the through-plane thickness 20 can be calculated mathematically at any chosen point, given the distance from the point of contact (or spacer 28). The through-plane thickness 20 can also be determined using optical techniques including, but not limited to, interferometry, confocal microscopy, or the like. A more complete description of methods of determining the through-plane thickness 20 can be found in U.S. patent application Ser. No. 09/248,135, filed Feb. 10, 1999. Regardless of which method is used, the chamber through-plane thickness 20 can be fixed and noted during the chamber 10 manufacturing process, or the through-plane thickness 20 can be determined at a later point in time prior to inserting the sample, or after the sample is inserted (e.g., at the end user's). In general, the size of the target constituent and the hematocrit of the sample dictate the most advantageous through-plane thickness 20. The relationship between constituents and through-plane thickness 20 will be discussed in detail below.

The whole blood sample is admixed with an amount of at least one sensible colorant sufficient to allow the visualization of the cells or particulates. The sensible colorant may be any material that: 1) distinguishes the target constituent within the whole blood sample; and 2) does not substantially dilute the whole blood sample when admixed. An example of a sensible colorant is a fluorescent highlighting supravital stain such as acridine orange, basic orange-21, or a similar dye that can be seen using a fluorescent microscope. In some instances, a single colorant may be used to identify several constituents. In other instances, a plurality of colorants may be used to distinguish a plurality of constituents. Other constituent evaluations, such as those described in U.S. patent application Ser. No. 09/249,721, filed Feb. 12,1999, may be simultaneously performed by the addition of another sensible colorant. The addition of the sensible colorant may be performed by adding a small quantity of the colorant in liquid form to the sample of whole blood, thus creating a minimal dilution of the sample, or the colorant may be added in a dried form such as a small tablet. An alternate means of admixing the sensible colorant to the whole blood sample is to dry the colorant on an area of the sample chamber 10. When the whole blood sample is inserted into the chamber 10, the colorant diffuses into the sample.

An amount of admixed whole blood sample large enough to contact both chamber walls 16,18 is inserted into the chamber 10. The sample may be inserted into the chamber 10 by a variety of means including the use of a bladder, capillary action, etc. Methods and apparatus which minimize the potential for the sample to spill are preferred for environmental and safety reasons.

Figure 5:
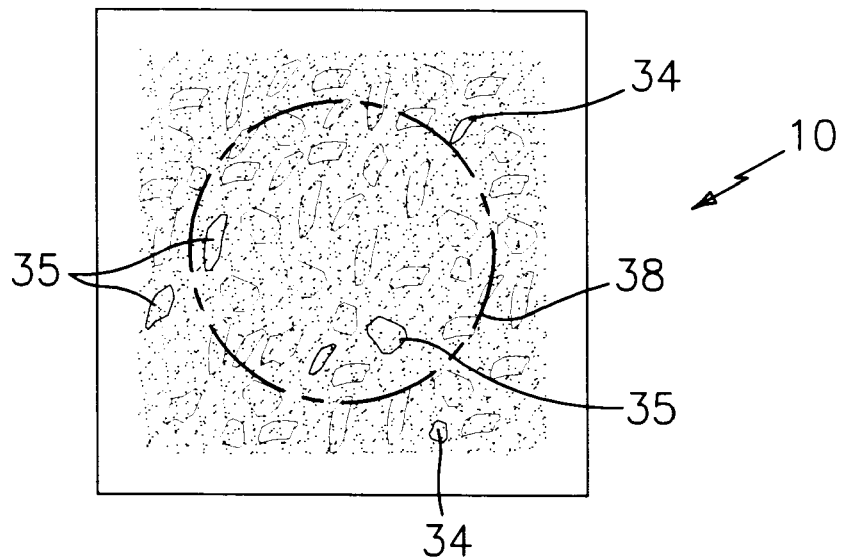
FIG. 5 is a diagrammatic view of a sample chamber illustrating the visual opaque appearance of a substantially undiluted, anti-coagulated whole blood sample before rouleaux and lacunae have formed.
Figure 6:
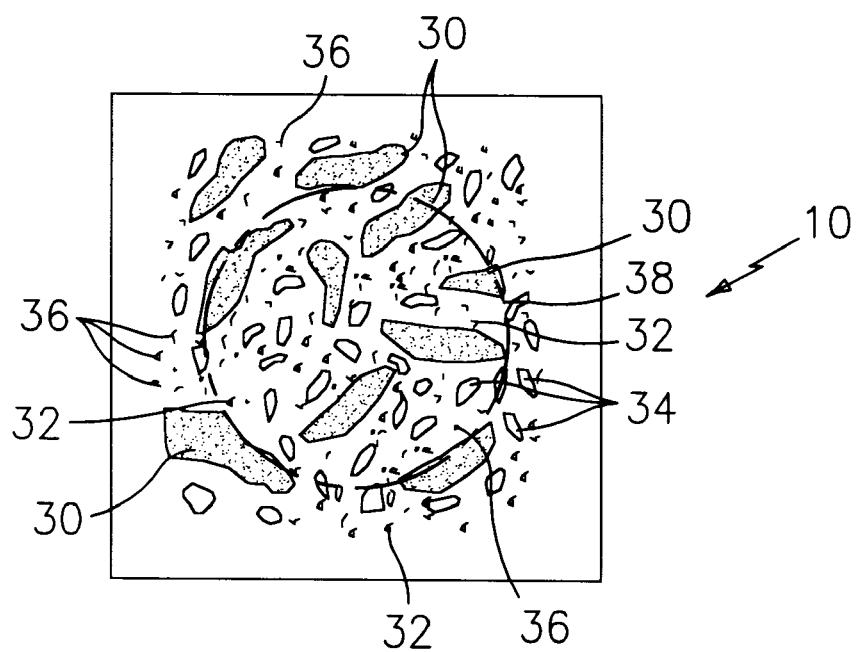
FIG. 6 is a diagrammatic view of a sample chamber illustrating the appearance of rouleaux and lacunae within a substantially undiluted, anti-coagulated whole blood sample formed after a quiescent period within the chamber.
Figure 1:
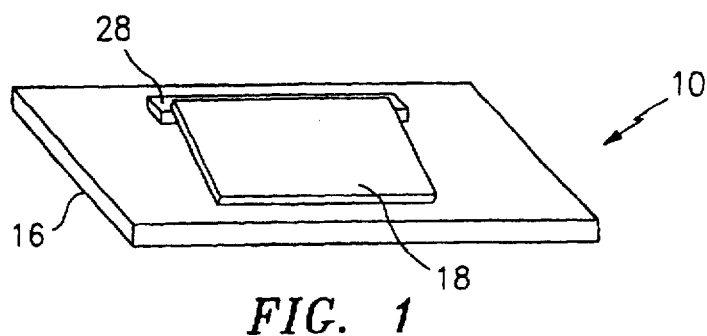
Figure 2:
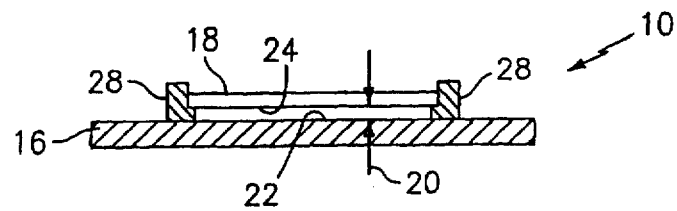
Figure 3:
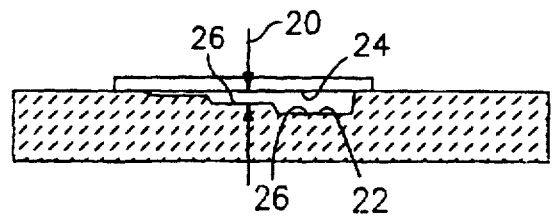
Figure 4:
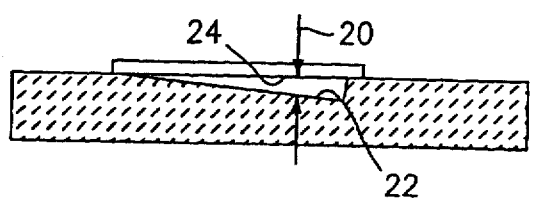

Referring to FIGS. 5 and 6, after admission into the chamber 10, the sample is held quiescently for a brief period of time to permit the formation of rouleaux 30 and lacunae 32 (see FIG. 6). As stated earlier, the only motion in the blood sample will be Brownian motion of the sample's formed constituents, which motion is not disabling of the use of the device of this invention. The rouleaux 30 are clusters of red blood cells (RBC's) that spontaneously form in substantially motionless, anti-coagulated whole blood. The lacunae are the open areas left between the rouleaux 30. Rouleaux 30 and lacunae 32 formation occurs naturally in anti-coagulated whole blood since the attractive forces that aggregate the RBC's force the other constituents, such as WBC's 34 and platelets 36 (see FIG. 6), into the lacunae 32 where they can be evaluated. Keeping a whole blood sample substantially motionless for approximately 15–30 seconds is usually adequate to permit rouleaux 30 and lacunae 32 formation, but the time can vary from sample to sample. The formation of rouleaux 30 can also be expedited by known aggregation agents, in which case clumps of RBC's would be referred to as aggregates. Examples of such aggregating agents are dextran, polybrene and mixtures of the two, antibodies against common red cell antigens, and vegetable lectins and the like.

The through-plane thickness 20 of the whole blood sample being evaluated is critical in evaluating the sample constituents. For example, if a $100\mu$ ($1\mu=1\times10^{-6}$ meters) thick layer of substantially undiluted anti-coagulated whole blood is examined via a microscope, the sample will appear opaque (as illustrated in FIG. 5) because light cannot adequately penetrate the layer, regardless of whether the RBC's are allowed to form rouleaux 30. If, however, the sample layer thickness is reduced to approximately less than $70\mu$, and preferably reduced to between $4\mu$ and $50\mu$, a sufficient amount of light will pass through such that the lacunae 32 appear as clear lakes within which WBC's 34 and platelets 36 can be distinguished and evaluated. The optimum sample layer thickness to enable the evaluation of constituents within the lacunae 32 will depend upon the original hematocrit of the sample. The hematocrit, which refers to the number of RBC's as a percentage of the total blood volume, is inversely related to the optimum sample layer thickness; i.e., a higher than typical hematocrit generally is associated with a thinner than typical optimum sample layer. In all cases, however, the sample layer must be thick enough to provide a reasonable number of particles or cells. Note that not every single constituent of interest may be forced into the lacunae 32. It is not disabling of this invention if a statistically or clinically insignificant number of the constituents are obscured by the RBC aggregates. It is also possible for one or more constituents of interest to lie on top of an aggregation of RBC's, but since these constituents will be visible (in the case of a vertical microscope), they will be fully evaluable by fluorescence.

The target constituent can be evaluated using a variety of techniques. If, for example, the target constituent is colored with a fluorescent dye, the lacunae 32 can be examined with a commercially available fluorescence microscope. The fluorescence microscope will illuminate the fluorescent dye interacting with the target constituent, thereby distinguishing it within the sample. The image produced with the fluorescence microscope can be recorded in an image dissector (e.g., a CCD camera) and that image can be manually evaluated, or the image can be digitized and stored in an electronic file. The electronic file can be interpreted using analysis software that has the ability, for example, to identify particular constituents, enumerate the occurrences of a particular constituent, and evaluate characteristics of the constituent. An example of commercially available analysis software is that sold by the Signal Analytics Corporation of Vienna, Va., U.S.A., or other such image processing systems. A more complete description of such an image evaluation system is provided in applicant's co-pending U.S. patent application Ser. No. 09/255,673, filed Feb. 23, 1999.

The following examples will illustrate how individual whole blood sample constituents can be evaluated using the present invention method and apparatus:

EXAMPLE I

Referring to FIGS. 5 and 6, WBC's 34 within an anti-coagulated whole blood sample admixed with a small quantity of a sensible colorant can be evaluated in a sample chamber 10 having a through-plane thickness 20 (see FIGS. 2–4), throughout the chamber 10 or in a portion of the chamber 10, approximately equal to $20\mu$. EDTA is an example of an anti-coagulating agent that may be used and a fluorescent highlighting supravital stain such as acridine orange, basic orange-21, or the like are examples of sensible colorants that may be used. A chamber through-plane thickness 20 of approximately $20\mu$ is chosen for a couple of reasons. First, the evaluation volume contains a useful number of WBC's 34 for examination, and second, a through-plane thickness 20 of $20\mu$ typically provides an optimal chamber for rouleaux 30 formation. The volume of sample being evaluated is typically defined by the cross-sectional area of the evaluative field 38 and the through-plane thickness 20 of the sample. As stated earlier, the exact through-plane thickness 20 of a field 38 within the chamber 10 may be optimized using several techniques, including iterative processes wherein the population of a target constituent within a particular field 38 is evaluated statistically and other fields 38 evaluated if necessary to increase or decrease the population.

FIG. 5 depicts a field 38 of the sample immediately after insertion into the chamber 10 at which time the sample appears opaque when examined either with transmitted light, or more preferably by epi-illuminated fluorescence. The opaque appearance is caused by the RBC's 35, which form an overlapping mass prior to the formation of the rouleaux 30. Despite the opaque appearance of the sample field 38, the colorant allows some WIC's 34 to be faintly distinguished. FIG. 6 shows the same chamber 10 after lying substantially motionless for approximately thirty (30) seconds. The RBC's 35 have spontaneously clustered into rouleaux 30, leaving lacunae 32 between the rouleaux 30. It is in these lacunae 32 where the other whole blood sample constituents (e.g., WBC's 34 and platelets 36) can be distinguished and evaluated. If a WBC 34 count is desired, a field 38 having a cross-sectional area of one square millimeter within the region of the chamber 10 having a through-plane thickness 20 of $20\mu$ (which contains 0.02 $\mu$l volume of whole blood sample) can be evaluated. A $0.02\mu$ sample is chosen to keep the number of WBC's 34 reasonable; a normal whole blood sample contains approximately 7,000 WBC's per $\mu$ of sample and a 0.02 $\mu$l sample of normal whole blood contains approximately 140 WBC's. A number of these fields 38 would be counted until enough cells are counted to get a number that has sufficient statistical accuracy, which in practice is approximately 1000 cells. If additional WBC 34 information is sought, the WBC's 34 (lymphocytes, granulocytes, monocytes, etc.) can be further evaluated within the chamber volume. For example, if it were desirable to classify the types of WBC's 34 within the whole blood sample and/or their frequency, the WBC's could be evaluated using an image dissector with/without analysis software. A differential count could be determined from the data collected. A more complete description of this method is given in co-pending U.S. patent application Ser. No. 09/252,153, filed Feb. 18, 1999.

If the lacunae 32 regions of the sample appear partially opaque at a chamber through-plane thickness of $20\mu$, perhaps as a result of a higher than typical hematocrit, it may be desirable to evaluate a sample field 38 within the sample chamber 10 having a through-plane thickness less than $20\mu$. On the other hand, if the hematocrit of the sample is lower than typical, it may be advantageous to use a sample field 38 having a through-plane thickness 20 greater than $20\mu$ because the population of each constituent is likely to be greater. The through-plane thickness 20 of the sample can also be changed as a method for increasing or decreasing the constituent populations.

EXAMPLE II

Platelets 36 within an anti-coagulated whole blood sample can be evaluated using the technique described in Example I. Because platelets are present in much greater quantity than WBC's 34, a chamber region having a through-plane thickness 20 approximately $5\mu$ in magnitude is used. Each field 38 having a cross-sectional area of one square millimeter within the chamber region having a through-plane thickness of $5\mu$ represents a sample volume of $0.005\mu$ and in a normal individual will therefore contain about 1250 platelets 36. The platelets 36 may be evaluated using the same fluorescent highlighting supravital stains and techniques as used for the WBC's 34. The platelets 36 may be evaluated in the same chamber 10 as that used to evaluate the WBC's, provided the chamber has regions of varying through-plane thickness magnitude such as those described above with skewed, stepped, and/or arcuate walls.

Although this invention has been shown and described with respect to the detailed embodiments thereof, it will be understood by those skilled in the art that various changes in form and detail thereof may be made without departing from the spirit and the scope of the invention. For example, the sample chamber is described as having a first wall and a transparent second wall. If transmittance is used instead of fluorescence as a mechanism for sensing the sample, then both the first wall and the second wall would be transparent.

What is claimed is:

1. A method for evaluating white blood cell constituents and/or platelet constituents in a substantially undiluted anticoagulated whole blood sample, said method comprising the steps of:

a) providing a sample chamber which is formed between a first wall and a transparent second wall, said walls being separated by a first through-plane thickness in a first region of said chamber;

b) creating an admixture of a colorant and the blood sample, wherein said colorant differentiates one or more of said constituents in the blood sample, said admixture being created either outside of, or inside of said chamber, and said admixture being in contact with said first and second walls of said chamber in said first region of said chamber when the admixture is inside of said chamber;

c) quiescently holding said admixture in said chamber for a predetermined time period sufficient to form one or more rouleaux, which rouleaux are contiguous with lacunae which also form within said quiescent admixture, and wherein said constituents reside within said lacunae;

d) examining one or more fields of view which are located within said first region of said chamber; and e) evaluating said white blood cell constituents and/or said platelet constituents present in said lacunae in said fields of view.

2. The method of claim 1, further comprising the step of selectively locating one or more fields in a second region of said chamber, said second region having a second through-plane thickness that is greater than said first through-plane thickness in said first region of said chamber.

3. The method of claim 1, further comprising the step of selectively locating one or more fields in a second region of said chamber, said second region having a second through-plane thickness that is less than said first through-plane thickness in said first region of said chamber.

4. The method of claim 1, wherein said first through-plane thickness is no greater than $70\mu$.

5. The method of claim 1 wherein said first through-plane thickness is no less than $4\mu$.

6. The method of claim 1 wherein said first through-plane thickness is no greater than $50\mu$.

7. The method of claim 1, wherein said admixture is created outside of said chamber.

8. The method of claim 1, wherein said said admixture is created inside of said chamber.

* * * * *

UNITED STATES PATENT AND TRADEMARK OFFICE
CERTIFICATE OF CORRECTION

PATENT NO. : 5,948,686
DATED : September 7, 1999
INVENTOR(S) : Stephen C. Wardlaw It is certified that error appears in the above-identified patent and that said Letters Patent is hereby corrected as shown below:

On the title page: Item [73]

after "Assignee:", please delete "Robert A. Leuine" and insert--Robert A. Levine--.

Signed and Sealed this

Twenty-fifth Day of April, 2000

Attest:

Q. TODD DICKINSON

Attesting Officer     Director of Patents and Trademarks

UNITED STATES PATENT AND TRADEMARK OFFICE
CERTIFICATE OF CORRECTION

Figure 2:
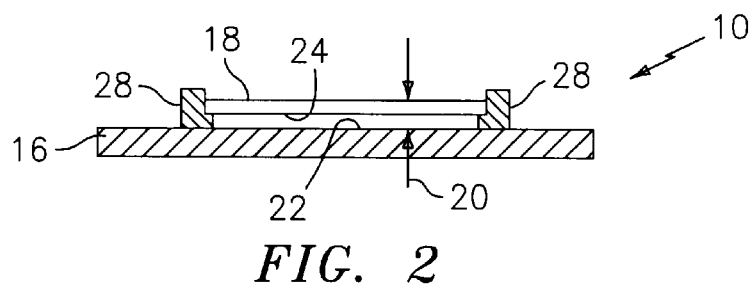
FIG. 2 is a diagrammatic cross-sectional view of a sample chamber which includes an inclined flat second wall. A through-plane thickness gradient is formed between the first and second walls.
Figure 3:
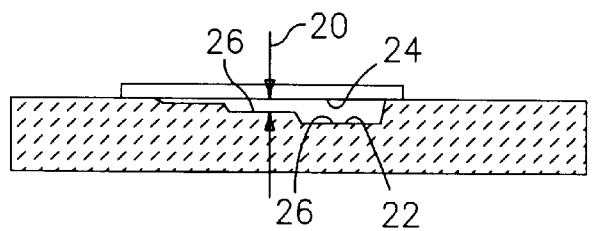
FIG. 3 is a diagrammatic cross-sectional view of a sample chamber which includes a flat second wall positioned over a first wall having a plurality of steps. The plurality of steps provide a plurality of chamber regions at different through-plane thicknesses.

PATENT NO. : 5,948,686
DATED : September 7, 1999
INVENTOR(S) : Stephen C. Wardlaw It is certified that error appears in the above-identified patent and that said Letters Patent is hereby corrected as shown below:

In the Drawing:
In Fig. 2, the upper arrowhead for reference numeral 20 is amended in corrected Fig. 2 to point to surface 24.

Figure 4:
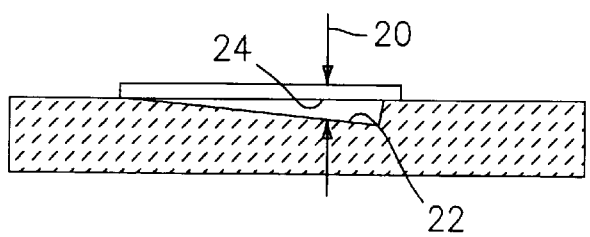
FIG. 4 is a diagrammatic cross-sectional view of a sample chamber having a flat second wall positioned over a first wall having a surface extending at an angle to the second wall. A through-plane thickness gradient is formed between the first and second walls.

In Fig. 4, the upper arrowhead for reference numeral 20 is amended in corrected Fig. 4 to point to surface 24.

Signed and Sealed this

Third Day of July, 2001

*Nicholas P. Godici*

Attest:

*Attesting Officer*

NICHOLAS P. GODICI
*Acting Director of the United States Patent and Trademark Office*